(12) United States Patent
Quinn et al.

(10) Patent No.: US 9,931,487 B2
(45) Date of Patent: Apr. 3, 2018

(54) BIDIRECTIONAL STEERING CONTROL APPARATUS FOR A CATHETER

(71) Applicant: Boston Scientific Scimed Inc., Maple Grove, MN (US)

(72) Inventors: William Quinn, Swampscott, MA (US); Kurt E. Guggenberger, North Andover, MA (US); Ian Collier, Newton, MA (US); Justin Callaway, Goffstown, NH (US); Doron Harlev, Brookline, MA (US); Paul DiCesare, Shelton, CT (US); Jeffrey P. Radziunas, Wallingford, CT (US); Greg Hires, Shelton, CT (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 11 days.

(21) Appl. No.: 15/229,691

(22) Filed: Aug. 5, 2016

(65) Prior Publication Data

US 2017/0035993 A1    Feb. 9, 2017

Related U.S. Application Data

(60) Provisional application No. 62/202,139, filed on Aug. 6, 2015.

(51) Int. Cl.
*A61M 25/01* (2006.01)
*A61B 17/00* (2006.01)
(Continued)

(52) U.S. Cl.
CPC ... *A61M 25/0147* (2013.01); *A61B 17/00234* (2013.01); *A61M 25/0136* (2013.01);
(Continued)

(58) Field of Classification Search
CPC .......... A61M 25/0147; A61M 25/0136; A61B 17/00234; A61B 5/0422; A61B 5/6852; A61B 2017/00326
(Continued)

(56) References Cited

U.S. PATENT DOCUMENTS

| 5,327,905 A | 7/1994 | Avitall |
| 5,364,351 A | 11/1994 | Heinzelman et al. |

(Continued)

FOREIGN PATENT DOCUMENTS

| EP | 1902746 B1 | 6/2009 |
| EP | 1895886 B1 | 3/2010 |

(Continued)

*Primary Examiner* — Paula J Stice
(74) *Attorney, Agent, or Firm* — Faegre Baker Daniels LLP (57) ABSTRACT

A steering control apparatus includes a first wire and a second wire extending from a distal end of a catheter to a steering assembly. The steering assembly includes a steering knob disposed at an exterior of the handle, a cylindrical steering shaft projecting from the steering knob and into the interior of the handle, a first cylindrical drum disposed within the handle and connected to the first wire, and a second cylindrical drum within the handle and connected to the second wire. The first drum is configured to engage the steering shaft to produce tension on the first wire. The first drum is coaxial with the steering shaft. The second drum is configured to engage the steering shaft to produce tension on the second wire. The second drum is coaxial with the steering shaft and axially adjacent to the first drum.

20 Claims, 9 Drawing Sheets

(51) Int. Cl.
  *A61B 5/00*     (2006.01)
  *A61B 5/042*    (2006.01)
(52) U.S. Cl.
  CPC .......... *A61B 5/0422* (2013.01); *A61B 5/6852* (2013.01); *A61B 2017/00323* (2013.01)
(58) Field of Classification Search
  USPC .............................. 607/115–116; 606/34, 41
  See application file for complete search history.

(56) References Cited

U.S. PATENT DOCUMENTS

| | | | |
|---|---|---|---|
| 5,456,664 A | 10/1995 | Heinzelman et al. | |
| 5,471,982 A | 12/1995 | Edwards et al. | |
| 5,681,280 A | 10/1997 | Rusk et al. | |
| 5,891,088 A | 4/1999 | Thompson et al. | |
| 6,029,091 A | 2/2000 | de la Rama et al. | |
| 6,461,356 B1 | 10/2002 | Patterson | |
| 6,652,506 B2 | 11/2003 | Bowe et al. | |
| 7,269,453 B2 | 9/2007 | Mogul | |
| 7,465,288 B2 | 12/2008 | Dudney et al. | |
| 8,348,888 B2 | 1/2013 | Selkee | |
| 8,447,377 B2 | 5/2013 | Harlev et al. | |
| 8,460,237 B2 | 6/2013 | Schultz | |
| 8,480,658 B1 | 7/2013 | Nakao | |
| 8,523,808 B2 | 9/2013 | Selkee | |
| 8,617,087 B2 | 12/2013 | Schultz | |
| 8,696,620 B2 | 4/2014 | Tegg | |
| 8,747,351 B2 | 6/2014 | Schultz | |
| 8,771,267 B2 | 7/2014 | Kunis et al. | |
| 8,808,345 B2 | 8/2014 | Clark et al. | |
| 8,956,322 B2 | 2/2015 | Selkee | |
| 9,101,269 B2 | 8/2015 | Selkee | |

FOREIGN PATENT DOCUMENTS

| | | |
|---|---|---|
| EP | 2204208 A2 | 7/2010 |
| EP | 2289592 B1 | 10/2012 |
| EP | 2308540 B1 | 4/2014 |
| EP | 1833398 B1 | 7/2014 |
| EP | 2543409 B1 | 5/2015 |

BIDIRECTIONAL STEERING CONTROL APPARATUS FOR A CATHETER

CROSS-REFERENCE TO RELATED APPLICATION

This application claims priority to Provisional Application No. 62/202,139, filed Aug. 5, 2016, which is herein incorporated by reference in its entirety.

TECHNICAL FIELD

The present invention relates to steerable medical catheters for use inside a body. More specifically, the invention relates to controls for steering a catheter inside the body.

BACKGROUND

Medical catheters are widely used to provide access to locations within a body to treat diseases. Medical therapy devices may be connected to an end of the catheter and the catheter steered within the body to position the therapy device at the treatment location. For example, cardiac arrhythmias may be treated by the ablation of specific heart tissue found to be causing arrhythmia. Ablation may be performed by a number of techniques, including the local application of energy, for example, radio frequency energy, or by the application of cryogenic temperatures to the site of the problem tissue. An ablation electrode may be a therapy device at or near the end of the catheter for providing the radio frequency energy. An ablation balloon may be a therapy device at or near the end of the catheter to for providing the cryogenic temperatures.

The specific heart tissue responsible for arrhythmia in a patient may be identified by moving a mapping catheter having one or more electrodes around the interior of the heart and measuring cardiac signals to sense changes in the electrical fields. A map of the electrical conductivity of the heart may be formed from the measurements to identify abnormalities which may be candidates for ablation. Some mapping catheters are designed such that the electrodes may physically contact the heart wall, including flexible designs that are inserted in a compact form and later deployed into a basket-like array. Such an electrode array may be a therapy device at or near the end of the catheter for mapping the electrical conductivity of the heart.

Particularly useful steerable catheters are those in which the end with the therapy device may be deflected in two different directions. Such catheters require a steering control apparatus able to reliably deflect the end of the catheter in both directions.

SUMMARY

Example 1 is a steering control apparatus substantially contained within a handle at a proximal end of a catheter to control deflection of a distal end of the catheter, the distal end including a therapy device, the steering control apparatus including a first wire extending from the distal end of the catheter to within the handle, a second wire extending from the distal end of the catheter to within the handle, and a steering assembly. The steering assembly includes a steering knob disposed at an exterior of the handle, a cylindrical steering shaft projecting from the steering knob and into the interior of the handle, a first cylindrical drum disposed within the handle and connected to the first wire, and a second cylindrical drum within the handle and connected to the second wire. The first drum is configured to engage the steering shaft to produce tension on the first wire. The first drum is coaxial with the steering shaft. The second drum is configured to engage the steering shaft to produce tension on the second wire. The second drum is coaxial with the steering shaft and axially adjacent to the first drum. Rotation of the steering shaft by the steering knob in a counterclockwise direction steers the distal end of the catheter in the second direction by increasing tension on the first wire and decreasing tension on the second wire. Rotation of the steering shaft by the steering knob in a clockwise direction steers the distal end in the first direction by decreasing tension on the first wire and increasing tension on the second wire.

In Example 2, the apparatus of Example 1, wherein the steering shaft includes plurality of splines projecting from a radially outward-facing surface of the steering shaft, the splines oriented in an axial direction. The first drum includes a radially inward-facing surface and a plurality of splines projecting from the inward-facing surface, the splines oriented in an axial direction and configured to engage the plurality of splines on the external surface of the steering shaft to produce the tension on the first wire. The second drum includes a radially inward-facing surface and a plurality of splines on the inward-facing surface, the splines oriented in an axial direction and configured to engage the plurality of splines on the external surface of the steering shaft to produce the tension on the second wire.

In Example 3, the apparatus of either of Examples 1 or 2, wherein the first drum further includes a first recess formed in an axial-facing surface, and a first groove extending from the recess and circumferentially around a portion of a radially outward-facing surface of the first drum. The first wire includes a first lug connected to a proximal end of the first wire, wherein the first lug is disposed in the first recess and a portion of the first wire is disposed within a least a portion of the first groove to connect the first drum to the first wire.

In Example 4, the apparatus of Example 3, wherein the second drum further includes a second recess formed in an axial-facing surface, and a second groove extending from the recess and circumferentially around a portion of a radially outward-facing surface of the second drum. The second wire includes a second lug connected to a proximal end of the second wire, wherein the second lug is disposed in the second recess and a portion of the second wire is disposed within a least a portion of the second groove to connect the second drum to the second wire.

In Example 5, the apparatus of Example 4, wherein the axial-facing surface of the first drum including the first recess faces the axial-facing surface of the second drum including the second recess.

In Example 6, the apparatus of any of Examples 1-5, wherein the first drum is directly connected to the second drum.

In Example 7, the apparatus of any of Examples 1-6, wherein the steering knob and the steering shaft are integrally formed.

In Example 8, the apparatus of any of Examples 1-7, wherein the steering knob and the steering shaft are formed of a glass-filled polycarbonate polymer.

In Example 9, the apparatus of any of Examples 1-8, further including a brake assembly. The brake assembly includes a friction plate disposed on an interior surface of the handle, a brake clip configured to engage the first drum and the second drum, and a braking knob disposed at the exterior of the handle on a side of the handle opposite the steering knob. The braking knob includes a cylindrical braking shaft projecting from the braking knob and into the interior of the handle. The braking knob is configured to engage the brake clip, wherein rotation of the braking shaft by the braking knob in one of a clockwise direction and a counterclockwise direction increases a frictional force between the friction plate and one of an axially facing surface of the first drum and an axially facing surface of the second drum; and rotation of the braking shaft by the braking knob in the other one of the clockwise direction and the counterclockwise direction decreases the frictional force between the friction plate and the one of the axially facing surface of the first drum and the axially facing surface of the second drum.

In Example 10, the apparatus of Example 9, wherein the brake clip includes a cylindrical hub and at least one brake arm. The cylindrical hub includes a radially outward-facing surface and threads projecting from a radially inward-facing surface of the hub. The radially outward-facing surface facing a radially inward-facing surface of the steering shaft. The at least one brake arm extends radially outward from the hub and across the axially-facing surface of the second drum to the radially outward-facing surface of the second drum, axially from the radially outward-facing surface of the second drum to the radially outward-facing surface of the first drum, and radially inward from the radially outward-facing surface of the first drum and across a portion of the axially-facing surface of the first drum. The braking knob further includes threads projecting from a radially outward-facing surface of the braking shaft, wherein the threads of the braking shaft are configured to engage the threads of the hub.

In Example 11, the apparatus of either of Examples 9 or 10, wherein the braking knob and the braking shaft are integrally formed.

In Example 12, the apparatus of any of Examples 9-11, wherein the braking knob and the braking shaft are formed of a glass-filled polycarbonate.

In Example 13, the apparatus of any of Examples 9-12, wherein the brake clip is formed of a polyetherimide.

Example 14 is a catheter including an elongate catheter body extending from a proximal end to a distal end, a therapy device connected to the distal end of the catheter body, a handle connected to the proximal end of the catheter body, and a steering control apparatus of any of claims 1-13. The distal end is steerable in a first direction and a second direction. The second direction is different from the first direction.

In Example 15, the catheter of Example 14, wherein catheter is a cardiac mapping catheter and the therapy device includes a mapping electrode array.

Example 16 is a steering control apparatus substantially contained within a handle at a proximal end of a catheter to control deflection of a distal end of the catheter, the distal end including a therapy device, the steering control apparatus including a first wire extending from the distal end of the catheter to within the handle, a second wire extending from the distal end of the catheter to within the handle, and a steering assembly. The steering assembly includes a steering knob disposed at an exterior of the handle, a cylindrical steering shaft projecting from the steering knob and into the interior of the handle, a first cylindrical drum disposed within the handle and connected to the first wire, and a second cylindrical drum within the handle and connected to the second wire. The first drum is configured to engage the steering shaft to produce tension on the first wire. The first drum is coaxial with the steering shaft. The second drum is configured to engage the steering shaft to produce tension on the second wire. The second drum is coaxial with the steering shaft and axially adjacent to the first drum. Rotation of the steering shaft by the steering knob in a counterclockwise direction steers the distal end of the catheter in the second direction by increasing tension on the first wire and decreasing tension on the second wire. Rotation of the steering shaft by the steering knob in a clockwise direction steers the distal end in the first direction by decreasing tension on the first wire and increasing tension on the second wire.

In Example 17, the apparatus of Example 16, wherein the steering shaft includes plurality of splines projecting from a radially outward-facing surface of the steering shaft, the splines oriented in an axial direction. The first drum includes a radially inward-facing surface and a plurality of splines projecting from the inward-facing surface, the splines oriented in an axial direction and configured to engage the plurality of splines on the external surface of the steering shaft to produce the tension on the first wire. The second drum includes a radially inward-facing surface and a plurality of splines on the inward-facing surface, the splines oriented in an axial direction and configured to engage the plurality of splines on the external surface of the steering shaft to produce the tension on the second wire.

In Example 18, the apparatus of either of Examples 16 or 17, wherein the first drum further includes a first recess formed in an axial-facing surface, and a first groove extending from the recess and circumferentially around a portion of a radially outward-facing surface of the first drum. The first wire includes a first lug connected to a proximal end of the first wire, wherein the first lug is disposed in the first recess and a portion of the first wire is disposed within a least a portion of the first groove to connect the first drum to the first wire.

In Example 19, the apparatus of Example 18, wherein the second drum further includes a second recess formed in an axial-facing surface, and a second groove extending from the recess and circumferentially around a portion of a radially outward-facing surface of the second drum. The second wire includes a second lug connected to a proximal end of the second wire, wherein the second lug is disposed in the second recess and a portion of the second wire is disposed within a least a portion of the second groove to connect the second drum to the second wire.

In Example 20, the apparatus of Example 19, wherein the axial-facing surface of the first drum including the first recess faces the axial-facing surface of the second drum including the second recess.

In Example 21, the apparatus of any of Examples 16-20, wherein the first drum is directly connected to the second drum.

In Example 22, the apparatus of any of Examples 16-21, wherein the steering knob and the steering shaft are integrally formed.

In Example 23, the apparatus of any of Examples 16-22, further including a brake assembly. The brake assembly includes a friction plate disposed on an interior surface of the handle, a brake clip configured to engage the first drum and the second drum, and a braking knob disposed at the exterior of the handle on a side of the handle opposite the steering knob. The braking knob includes a cylindrical braking shaft projecting from the braking knob and into the interior of the handle. The braking knob is configured to engage the brake clip, wherein rotation of the braking shaft by the braking knob in one of a clockwise direction and a counterclockwise direction increases a frictional force between the friction plate and one of an axially facing surface of the first drum and an axially facing surface of the second drum; and rotation of the braking shaft by the braking knob in the other one of the clockwise direction and the counterclockwise direction decreases the frictional force between the friction plate and the one of the axially facing surface of the first drum and the axially facing surface of the second drum.

In Example 24, the apparatus of Example 23, wherein the brake clip includes a cylindrical hub and at least one brake arm. The cylindrical hub includes a radially outward-facing surface and threads projecting from a radially inward-facing surface of the hub. The radially outward-facing surface facing a radially inward-facing surface of the steering shaft. The at least one brake arm extends radially outward from the hub and across the axially-facing surface of the second drum to the radially outward-facing surface of the second drum, axially from the radially outward-facing surface of the second drum to the radially outward-facing surface of the first drum, and radially inward from the radially outward-facing surface of the first drum and across a portion of the axially-facing surface of the first drum. The braking knob further includes threads projecting from a radially outward-facing surface of the braking shaft, wherein the threads of the braking shaft are configured to engage the threads of the hub.

In Example 25, the apparatus of either of Examples 23 or 24, wherein the braking knob and the braking shaft are integrally formed.

Example 26 is a catheter including an elongate catheter body extending from a proximal end to a distal end, a therapy device connected to the distal end of the catheter body, a handle connected to the proximal end of the catheter body, and a steering control mechanism disposed at least partially within the handle. The distal end is steerable in a first direction and a second direction. The second direction is different from the first direction. The steering control mechanism includes a first wire extending from the distal end of the catheter to within the handle, a second wire extending from the distal end of the catheter to within the handle, and a steering assembly. The steering assembly includes a steering knob disposed at an exterior of the handle, a cylindrical steering shaft projecting from the steering knob and into the interior of the handle, a first cylindrical drum disposed within the handle and connected to the first wire, and a second cylindrical drum within the handle and connected to the second wire. The first drum is configured to engage the steering shaft to produce tension on the first wire. The first drum is coaxial with the steering shaft. The second drum is configured to engage the steering shaft to produce tension on the second wire. The second drum is coaxial with the steering shaft and axially adjacent to the first drum. Rotation of the steering shaft by the steering knob in a counterclockwise direction steers the distal end of the catheter in the second direction by increasing tension on the first wire and decreasing tension on the second wire. Rotation of the steering shaft by the steering knob in a clockwise direction steers the distal end in the first direction by decreasing tension on the first wire and increasing tension on the second wire In Example 27, the catheter of Example 26, wherein the steering shaft includes plurality of splines projecting from a radially outward-facing surface of the steering shaft, the splines oriented in an axial direction. The first drum includes a radially inward-facing surface and a plurality of splines projecting from the inward-facing surface, the splines oriented in an axial direction and configured to engage the plurality of splines on the external surface of the steering shaft to produce the tension on the first wire. The second drum includes a radially inward-facing surface and a plurality of splines on the inward-facing surface, the splines oriented in an axial direction and configured to engage the plurality of splines on the external surface of the steering shaft to produce the tension on the second wire.

In Example 28, the catheter of either of Examples 26 or 27, wherein the first drum further includes a first recess formed in an axial-facing surface, and a first groove extending from the recess and circumferentially around a portion of a radially outward-facing surface of the first drum. The first wire includes a first lug connected to a proximal end of the first wire, wherein the first lug is disposed in the first recess and a portion of the first wire is disposed within a least a portion of the first groove to connect the first drum to the first wire.

In Example 29, the catheter of Example 28, wherein the second drum further includes a second recess formed in an axial-facing surface, and a second groove extending from the recess and circumferentially around a portion of a radially outward-facing surface of the second drum. The second wire includes a second lug connected to a proximal end of the second wire, wherein the second lug is disposed in the second recess and a portion of the second wire is disposed within a least a portion of the second groove to connect the second drum to the second wire.

In Example 30, the catheter of Example 29, wherein the axial-facing surface of the first drum including the first recess faces the axial-facing surface of the second drum including the second recess.

In Example 31, the catheter of any of Examples 26-30, wherein the steering knob and the steering shaft are integrally formed.

In Example 32, the catheter of any of Examples 26-31, wherein the steering control mechanism further includes a brake assembly. The brake assembly includes a friction plate disposed on an interior surface of the handle, a brake clip configured to engage the first drum and the second drum, and a braking knob disposed at the exterior of the handle on a side of the handle opposite the steering knob. The braking knob includes a cylindrical braking shaft projecting from the braking knob and into the interior of the handle. The braking knob is configured to engage the brake clip, wherein rotation of the braking shaft by the braking knob in one of a clockwise direction and a counterclockwise direction increases a frictional force between the friction plate and one of an axially facing surface of the first drum and an axially facing surface of the second drum; and rotation of the braking shaft by the braking knob in the other one of the clockwise direction and the counterclockwise direction decreases the frictional force between the friction plate and the one of the axially facing surface of the first drum and the axially facing surface of the second drum.

In Example 33, the catheter of Example 32, wherein the brake clip includes a cylindrical hub and at least one brake arm. The cylindrical hub includes a radially outward-facing surface and threads projecting from a radially inward-facing surface of the hub. The radially outward-facing surface facing a radially inward-facing surface of the steering shaft. The at least one brake arm extends radially outward from the hub and across the axially-facing surface of the second drum to the radially outward-facing surface of the second drum, axially from the radially outward-facing surface of the second drum to the radially outward-facing surface of the first drum, and radially inward from the radially outward-facing surface of the first drum and across a portion of the axially-facing surface of the first drum. The braking knob further includes threads projecting from a radially outward-facing surface of the braking shaft, wherein the threads of the braking shaft are configured to engage the threads of the hub.

In Example 34, the catheter of either of Examples 32 or 33, wherein the braking knob and the braking shaft are integrally formed.

In Example 35, the catheter of any of Examples 16-34, wherein catheter is a cardiac mapping catheter and the therapy device includes a mapping electrode array.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

Catheters embodying the present invention may be employed in cardiac mapping catheters as described in "CARDIAC MAPPING CATHETER" (U.S. Pat. No. 8,447,377, issued May 21, 2013), hereby incorporated by reference in its entirety. Such catheters typically have several flexible splines forming an array at a distal end of the catheter, each spline including a plurality of electrodes. Catheter embodiments of the present invention include a steering control mechanism that controls deflection of the distal end in two different directions.

Figure 1A:
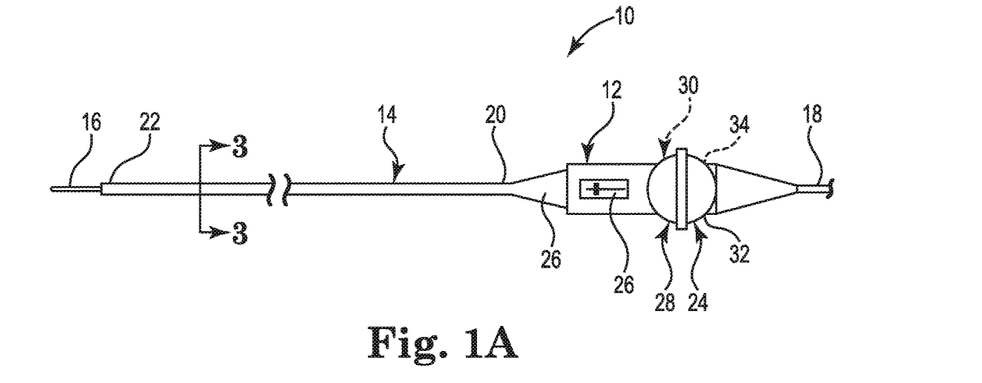
FIGS. 1A-1C are schematic views of a steerable catheter suitable for use with embodiments of the present invention.
Figure 1B:
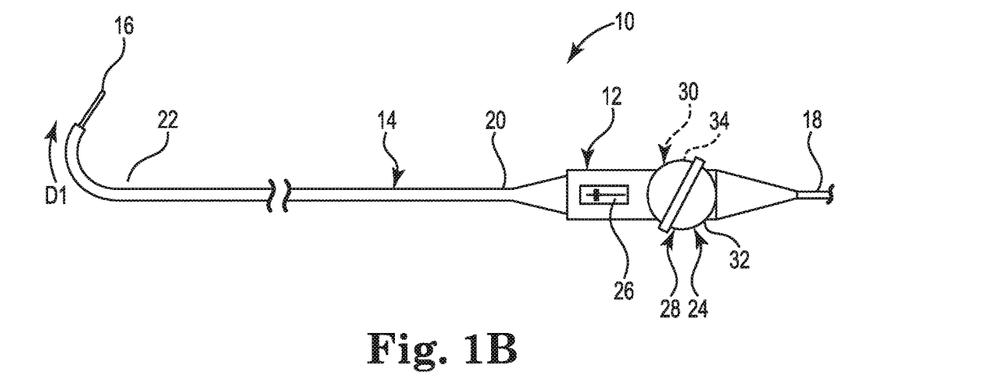
Figure 1C:
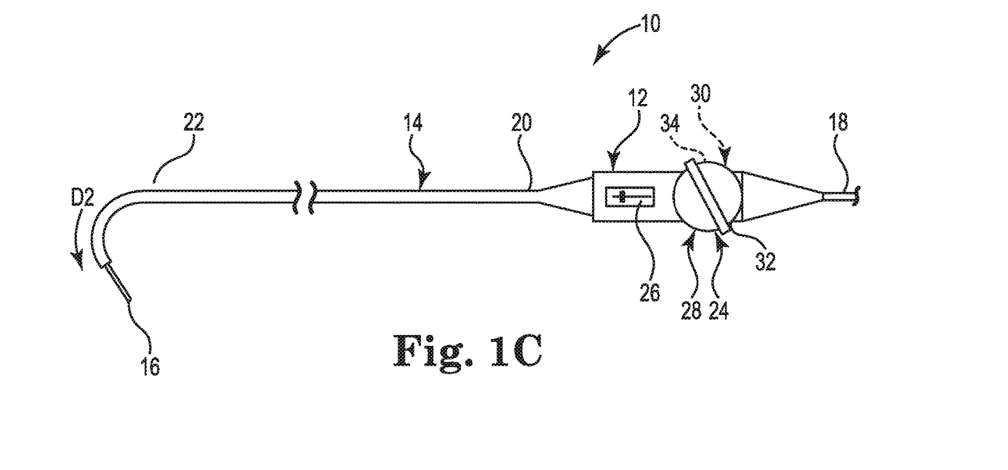

FIGS. 1A-1C provide an illustrative but non-limiting example of a catheter 10 including an embodiment of a steering control mechanism. As shown in FIGS. 1A-1C, the catheter 10 may include a handle 12, an elongate catheter body 14, a therapy device 16, and an electrical connection 18. The catheter body 14 may extend from a proximal end 20 to a distal end 22. The therapy device 16 may project from the distal end 22 of the catheter body 14. In one embodiment, the therapy device 16 includes a plurality of mapping electrodes. In one embodiment, the therapy device 16 is an expandable, splined mapping electrode assembly such as is disclosed in the aforementioned U.S. Pat. No. 8,447,377. In the illustrated embodiment, the therapy device 16 is shown in an undeployed configuration for ease of illustration.

In various embodiments, the therapy device 16 may include imaging elements, e.g., ultrasound transducers. In other embodiments, the therapy device 16 may be, for example, an ablation electrode. In various other embodiments, the therapy device 16 may have both therapeutic (e.g., ablation) capabilities as well as diagnostic (e.g., mapping, imaging, etc.) capabilities.

The catheter body 14 may be connected at the proximal end 20 to the handle 12. The electrical connection 18 may extend from the handle 12 to a mapping data recording and analysis system (not shown) and/or an ablation energy source (not shown), as the case may be.

The handle 12 may include a steering control mechanism 24 and a deployment control mechanism 26. The steering control mechanism 24 may include a steering assembly 28 and a brake assembly 30. The steering assembly 28 may include a steering knob 32. Although not illustrated in FIGS. 1A-1C, the brake assembly 30 may include a braking knob 34. The steering knob 32 is disposed at an exterior of the handle 12. The braking knob 34 may be disposed on the exterior of the handle 12 on a side of the handle 12 opposite the steering knob 32.

The deployment control 26 may control deployment of the electrode array 16 by way of a deployment control element (not shown) extending from the deployment control 26 to the therapy device 16 by way of one of the lumens extending through the catheter body 14. The lumens may also include a set of electrical conductors (not shown) extending from the therapy device 16 to handle 12 to connect the therapy device 16 to a processing unit (not shown), such as a mapping data recording and analysis system, or an ablation energy source.

The steering control mechanism 24 may control bending of the distal end 22 of the catheter body 14 by way of one or more wires 68, 88 (shown in FIGS. 3-6) The wires 68, 88 may extend from the steering control mechanism 24 within the handle 12 to the distal end 22 by way of one or more lumens (not shown) extending through the catheter body 14 from the proximal end 20 to the distal end 22. Bending the distal end 22 provides for flexibility in maneuvering the therapy device 16 within a patient's body.

FIGS. 1A-1C illustrate control of the deflection of the distal end 22 by the steering control mechanism 24. FIG. 1A shows the distal end 22 in an undeflected position with the steering knob 32 in a corresponding neutral position. FIG. 1B shows the steering knob 32 rotated in a direction clockwise from the neutral position to deflect the distal end 22 in a first direction D1. FIG. 1C shows the steering knob 32 rotated in a direction counterclockwise from the neutral position to deflect the distal end 22 in a second direction D2. As shown in FIGS. 1B and 1C, the second direction D2 is different from the first direction D1. The braking knob 34 may be rotated to vary a level of friction experienced through the steering knob 32 to provide smooth, comfortable operation of the steering assembly 28. Once the distal end 22 is deflected as desired, the braking knob 34 may be rotated to produce a level of friction sufficient to prevent movement of the steering knob 32 to maintain the deflection of the distal end 22.

Figure 2:
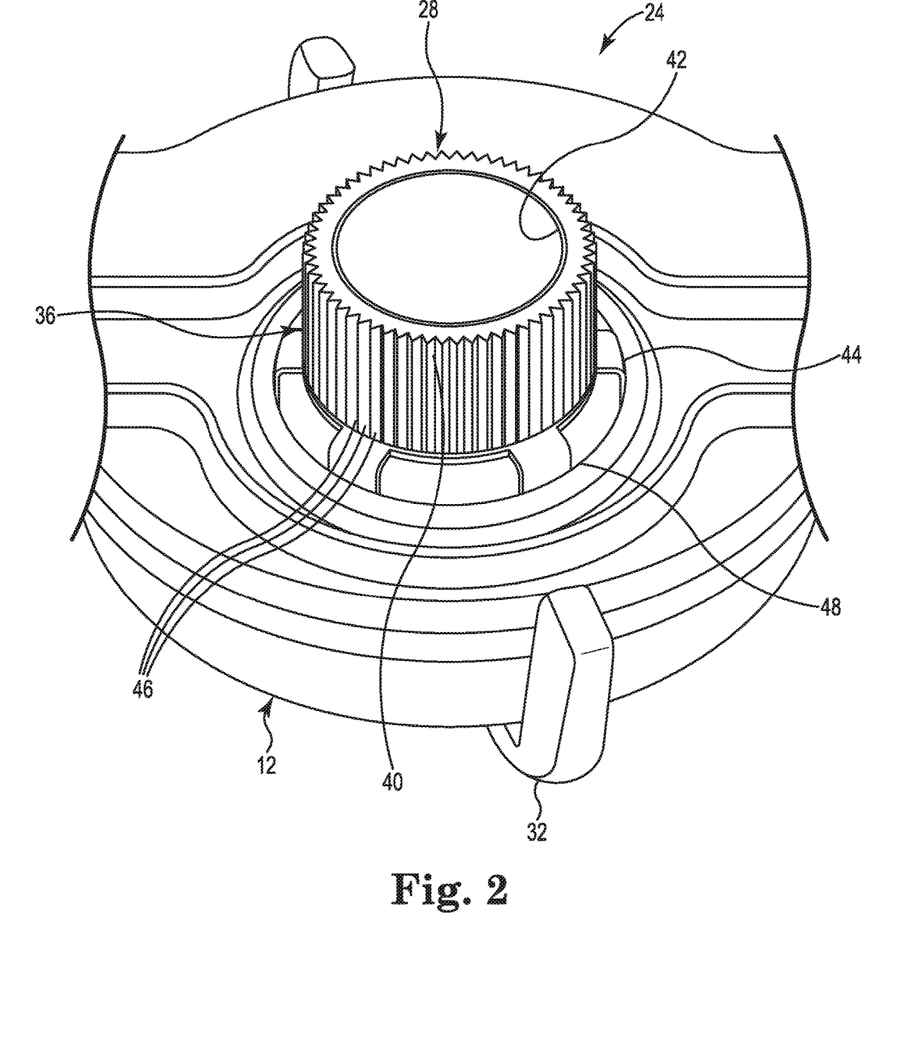
FIG. 2 is a partial perspective view showing a portion of a steering control apparatus within a catheter handle.

FIG. 2 is a partial perspective view showing a portion of the steering control apparatus 24 within the catheter handle 12. As shown in FIG. 2, the steering assembly 28 further includes a steering shaft 36. The steering shaft 36 has a cylindrical, tubular shaped structure and includes a radially outward-facing surface 40, a radially inward-facing surface 42, a plurality of bearing structures 44, and a plurality of splines 46. The bearing structures 44 project from the radially outward-facing surface 40. The bearing structures 44 position the steering shaft 36 within a hole 48 of the handle 12, while permitting free rotation of steering shaft 36 within the hole 48. The splines 46 project from the radially outward-facing surface 40 and are oriented in an axial direction of the steering shaft 36. The splines 46 may be substantially identical to each other and distributed evenly about the circumference of the steering shaft 36, as shown in FIG. 2. The steering shaft 36 is connected to, and projects from, the steering knob 32 and into the interior of the handle 12. Thus, rotation of the steering knob 32 rotates the steering shaft 36.

In some embodiments, the steering knob 32 and the steering shaft 36 may be made from a hard plastic, for example, a glass-filled polycarbonate or a polyoxymethylene. In some embodiments, the steering knob 32 and the steering shaft 36 may be integrally formed by, for example, injection molding, to form a single piece.

Figure 3:
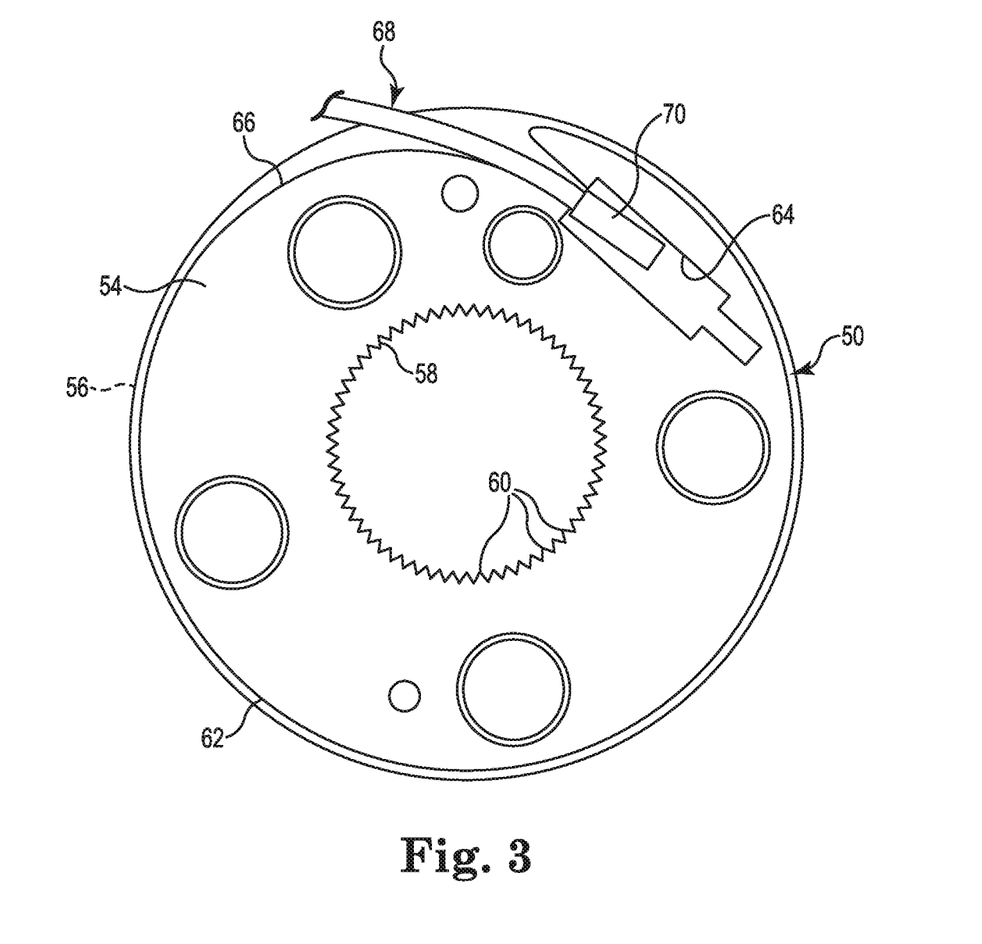
FIGS. 3, 4, and 5 are perspective views of another portion of the steering control apparatus.
Figure 4:
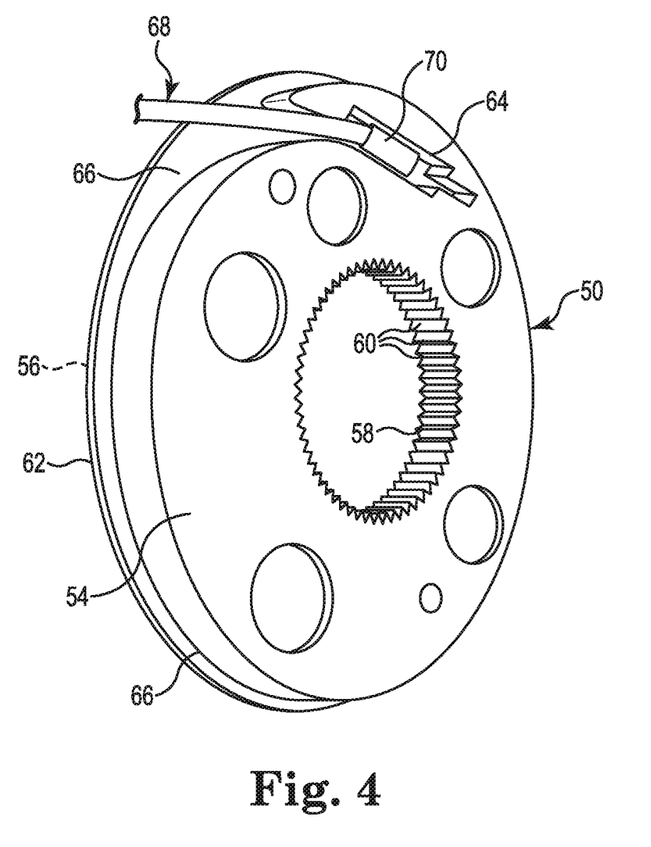
Figure 5:
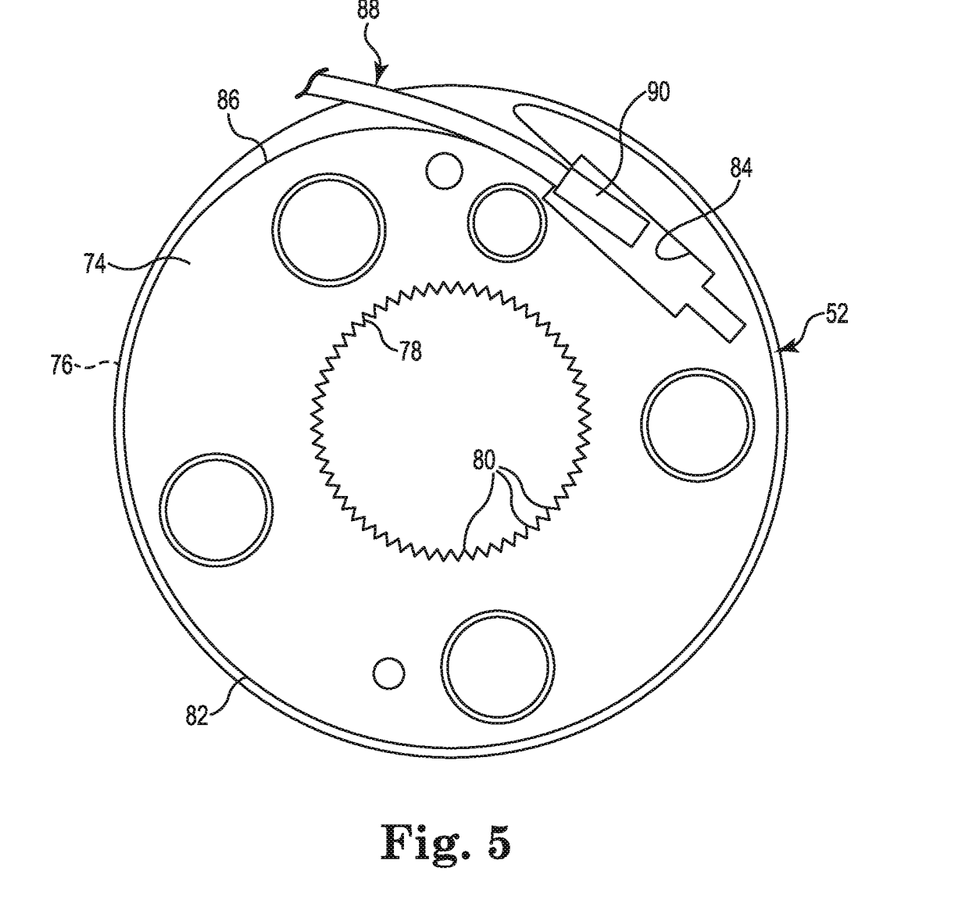

FIGS. 3, 4, and 5 are perspective views of another portion of the steering control apparatus 24. The steering assembly 28 further includes a first drum 50 shown in FIGS. 3 and 4, and a second drum 52 shown in FIG. 4. In some embodiments, the first drum 50 and the second drum 52 may be substantially identical, each having a flattened, disk-like cylindrical structure. As shown in FIG. 3, the first drum 50 includes a first axially-facing surface 54, a second axially-facing surface 56, a radially inward-facing surface 58, a plurality of splines 60, a radially outward-facing surface 62, a first recess 64, and a first groove 66. FIG. 3 also shows a proximal end of the first wire 68. The first wire 68 includes a first lug 70 connected to the proximal end of the first wire 68. The splines 60 project from the radially inward-facing surface 58 and are oriented in an axial direction of the first drum 50. The splines 60 may be substantially identical to each other and distributed evenly about the circumference of the first drum 50, as shown in FIG. 3. The first recess 64 is formed in the first axially-facing surface 54. The first lug 70 may be inserted into the first recess 64 as shown to connect the first wire 68 to the first drum 50.

FIG. 4 is another perspective view of the first drum 50 of FIG. 3. FIG. 4 shows that the first groove 66 extends from the first recess 64 and circumferentially around a portion of the radially outward-facing surface 62. Once assembled, a portion of the first wire 68 may be disposed within at least a portion of the first groove 66.

As shown in FIG. 5, the second drum 52 includes a third axially-facing surface 74, a fourth axially-facing surface 76, a radially inward-facing surface 78, a plurality of splines 80, a radially outward-facing surface 82, a second recess 84, and a second groove 86. FIG. 5 also shows a proximal end of the second wire 88. The second wire 88 includes a second lug 90 connected to the proximal end of the second wire 88. The splines 80 project from the radially inward-facing surface 78 and are oriented in an axial direction of the second drum 52. The splines 80 may be substantially identical to each other and distributed evenly about the circumference of the second drum 52, as shown in FIG. 5. The second recess 84 is formed in the third axially-facing surface 74. The second lug 90 may be inserted into the second recess 84 as shown to connect the second wire 88 to the second drum 52. As with the first drum 50, the second groove 86 extends from the second recess 84 and circumferentially around a portion of the radially outward-facing surface 82. Once assembled, a portion of the second wire 88 may be disposed within at least a portion of the second groove 86.

Figure 6:
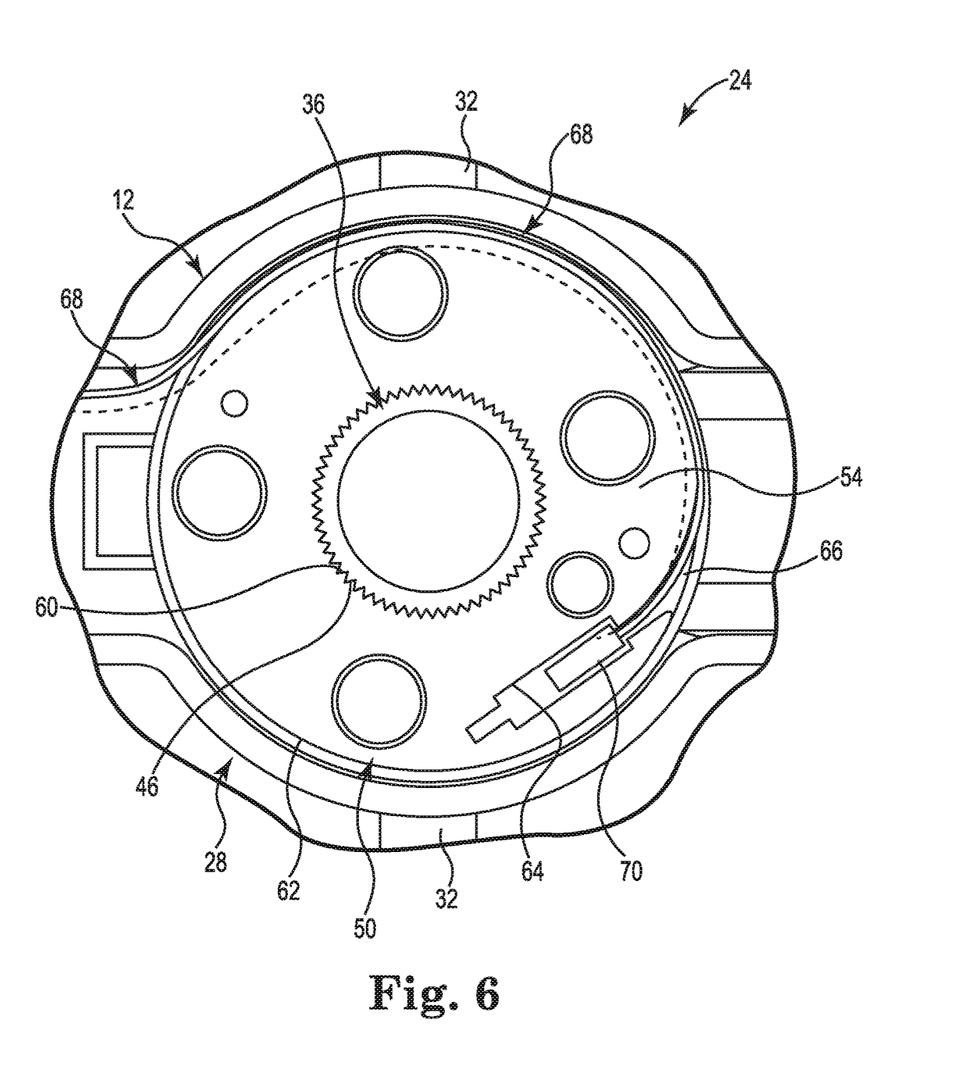
FIG. 6 is an axial view of a portion of the steering control apparatus within the catheter handle.

FIG. 6 is an axial view of a portion of the steering control apparatus 24 within the catheter handle 12. FIG. 6 shows the first drum 50 disposed within the handle 12 and engaged with the steering shaft 36 in a coaxial configuration. The splines 60 of the first drum 50 are configured to engage with the splines 46 of the steering shaft 36. Sliding the first drum 50 onto the steering shaft 36 in an axial direction engages the splines 60 with the splines 46. The first drum 50 may be rotated about its axis prior to sliding onto the steering shaft 36. The degree of rotation may be selected to provide a nominal tension on the first wire 68. The tension may be precisely controlled depending upon the number of splines 46 around the steering shaft 36 of the radially outward-facing surface 40, and the number of splines 60 around the radially inward-facing surface 58. Once the nominal tension is provided on the first wire 68, the first drum 50 is slid onto the steering shaft 36 while the distal end 22 is undeflected and the steering knob 32 in the corresponding neutral position, as shown in FIG. 1. The nominal tension on the first wire 68 may be maintained until the steering shaft 36 is rotated by the steering knob 32 to deflect the distal end 22.

In some embodiments, the first drum 50 and the second drum 52 may be made from a hard plastic, for example, a glass-filled polycarbonate or a polyoxymethylene. In some embodiments, the first drum 50 and the second drum 52 may be individually formed by, for example, injection molding.

Figure 7:
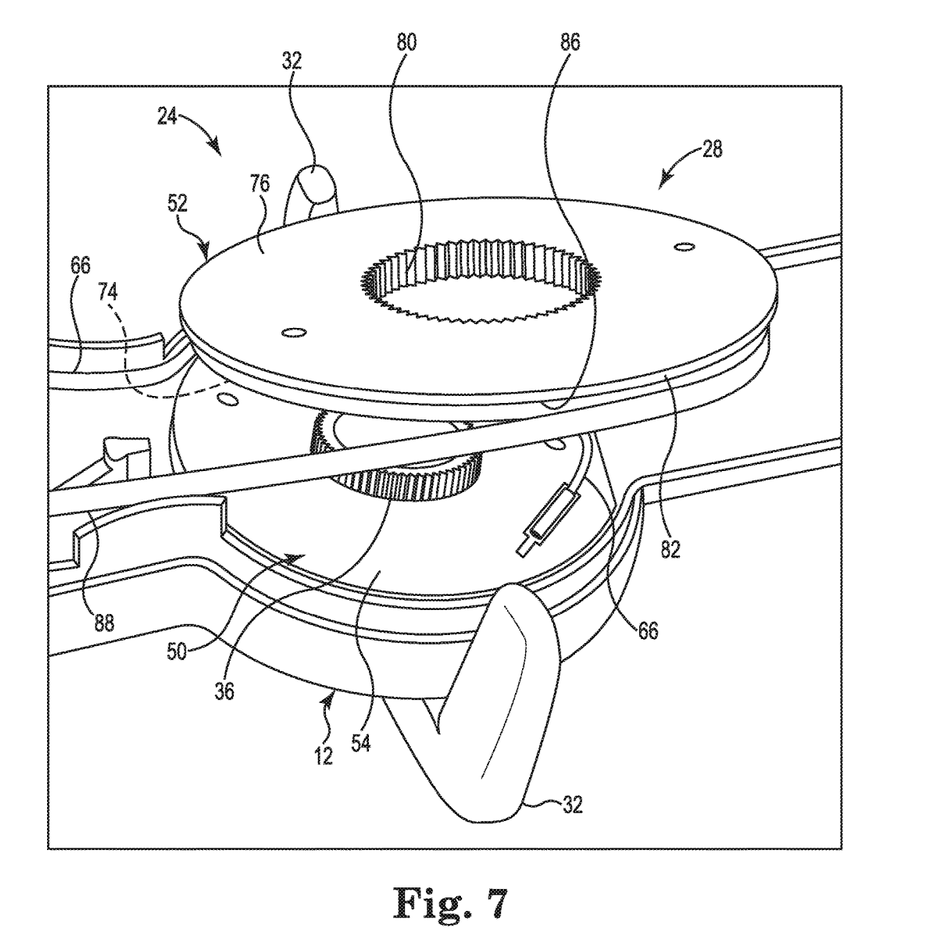
FIG. 7 is a partial perspective view of a portion of the steering control apparatus within the catheter handle.

FIG. 7 is a partial perspective view of a portion of the steering control apparatus 24 within the catheter handle 12. FIG. 7 shows the first drum 50 disposed within the handle 12 and connected to the first wire 66 as described above in reference to FIG. 6. FIG. 7 also shows the second drum 52 being placed within the handle 12. As with the first drum 50, the splines 80 of the second drum 52 are configured to engage with the splines 46 of the steering shaft 36. The second drum 52 may be slid onto the steering shaft 36 in an axial direction as the splines 80 engage with the splines 46. The second drum 52 may be slid down the length of the steering shaft 36 until the second drum 52 is axially adjacent to the first drum 50. The second drum 52 may be rotated about its axis prior to sliding onto the steering shaft 36. The degree of rotation may be selected to provide a nominal tension on the second wire 88. The tension may be precisely controlled depending upon the number of splines 46 around the steering shaft 36 of the radially outward-facing surface 40, and the number of splines 80 around the radially inward-facing surface 78. Once the nominal tension is provided on the second wire 88, the second drum 52 is slid onto the steering shaft 36 while the distal end 22 is undeflected and the steering knob 32 in the corresponding neutral position, as shown in FIG. 1. The nominal tension on the second wire 88 may be maintained until the steering shaft 36 is rotated by the steering knob 32 to deflect the distal end 22. Thus, with the steering control apparatus 24, a nominal tension may be quickly and easily provided on both the first wire 68 and the second wire 88.

Rotation of the steering shaft 36 by the steering knob 32 simultaneously changes the tension in the first wire 66 and the second wire 88 in a manner coordinated to steer or deflect the distal end 22, because both the first drum 50 and the second drum 52 are connected to the steering shaft 36. Thus, considering FIGS. 1B, 1C, and 7 together, rotation of the steering shaft 36 by the steering knob 32 in the counterclockwise direction (FIG. 1C), steers or deflects the distal end 22 in the second direction D2 by increasing tension on the first wire 66 and decreasing tension on the second wire 88. Conversely, rotation of the steering shaft 36 in the clockwise direction (FIG. 1B), steers or deflects the distal end 22 in the first direction D1 by decreasing the tension on the first wire 66 and increasing tension on the second wire 88.

In the embodiment shown in FIG. 7, the first drum 50 and the second drum 52 are disposed on the steering shaft 36 such that the first axially-facing surface 54 of the first drum 50 faces the third axially-facing surface 74 of the second drum 52. In this configuration, the first recess 64 faces the third axially-facing surface 74 to help contain the first lug 70 within the first recess 64; and the second recess 84 faces the first axially-facing surface 54 to help contain the second lug 90 within the second recess 84. In some embodiments, once the first drum 50 and the second drum 52 have been individually rotated to produce the nominal tensions on the first wire 66 and the second wire 88, respectively, and connected to the steering shaft 36, the first drum 50 may be directly connected to the second drum 52 by, for example, applying an adhesive between the first axially-facing surface 54 and the third axially-facing surface 74.

Figure 8:
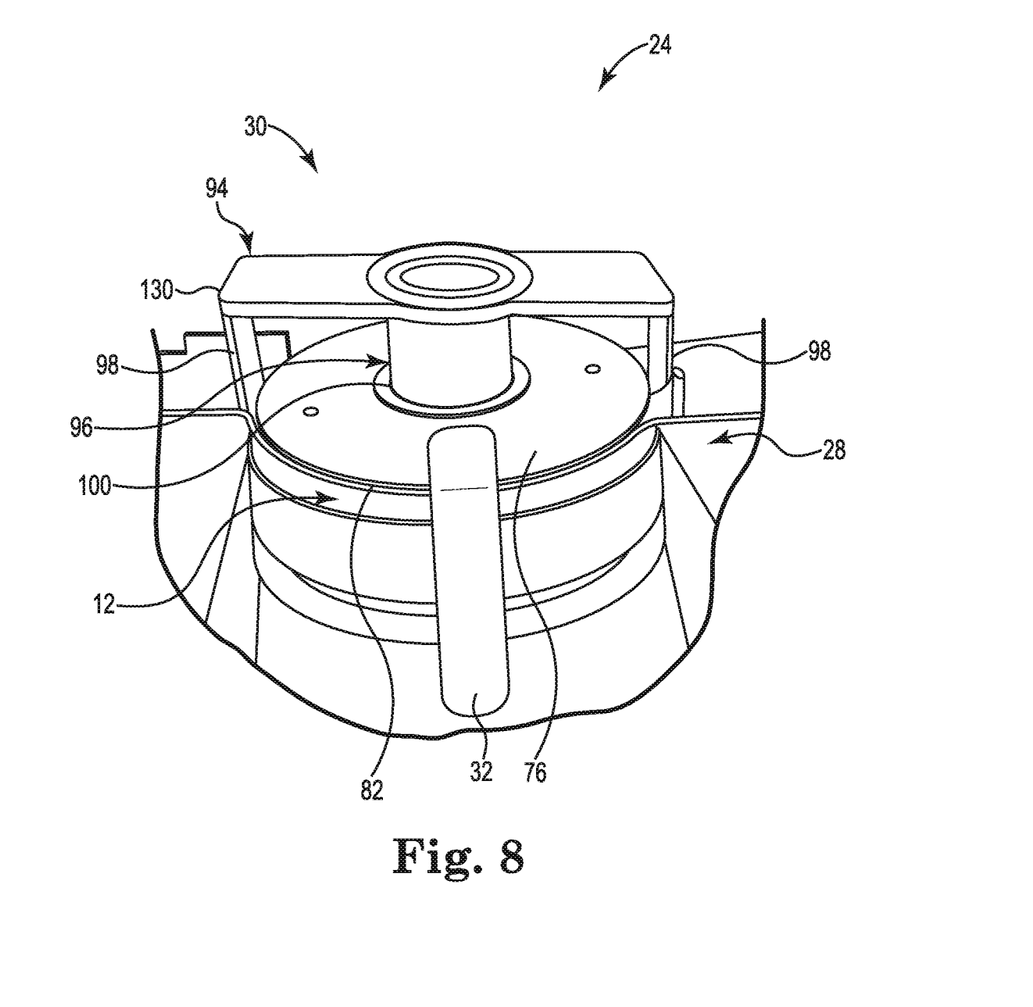
FIG. 8 is another partial perspective view of a portion of the steering control apparatus within the catheter handle.
Figure 9:
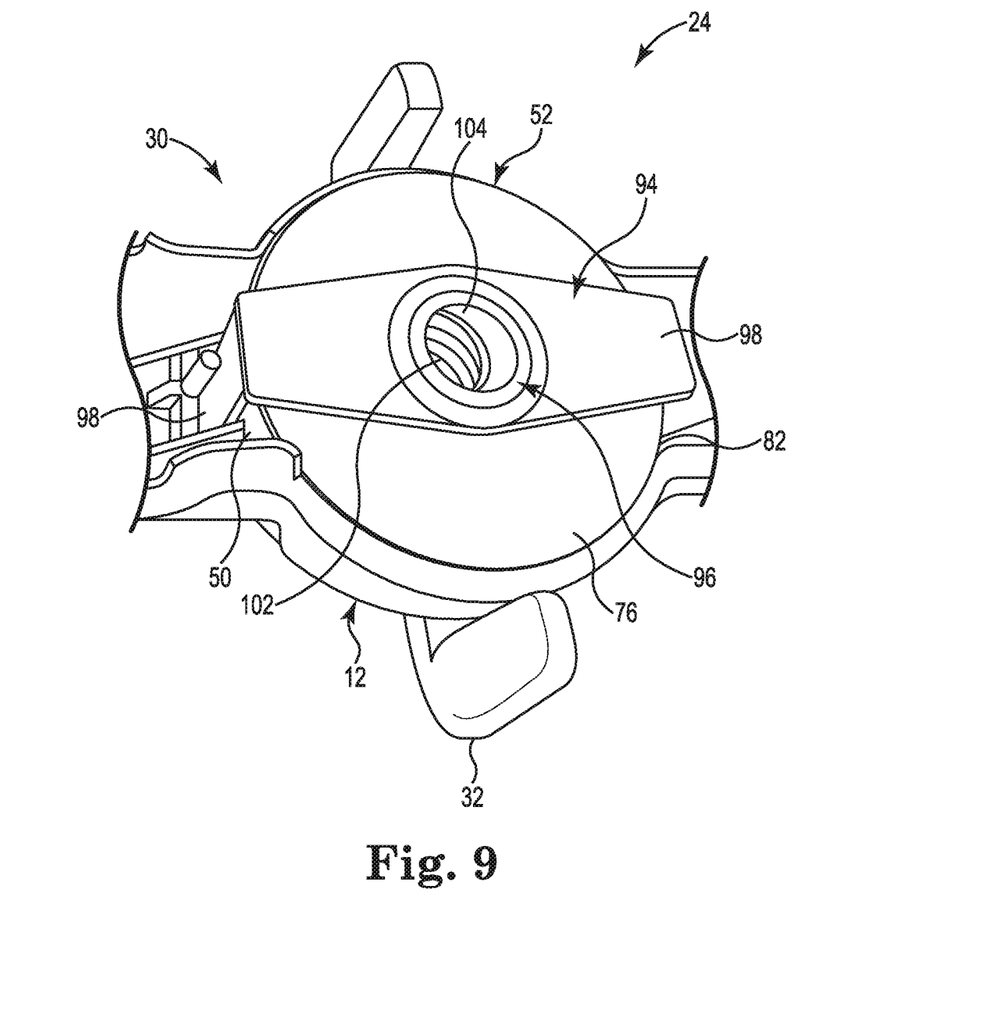
FIG. 9 is yet another partial perspective view of a portion of the steering control apparatus within the catheter handle.

FIGS. 8 and 9 are partial perspective views of a portion of the steering control apparatus 24 within the catheter handle 12 illustrating portions of the brake assembly 30. The brake assembly 30 further includes a friction plate 92 and a brake clip 94. Although the friction plate 92 is not illustrated, it is a plate of material having a relatively high coefficient of friction. The friction plate 92 is disposed in an interior surface of the handle 12. The brake clip 94 is configured to engage the first drum 50 and the second drum 52. FIG. 8 illustrates a portion of the steering control apparatus 24 before the brake clip 94 is installed around the first drum 50 and the second drum 52. FIG. 9 illustrates the portion of the steering control apparatus 24 showing the brake clip 94 installed around the first drum 50 and the second drum 52. Considering FIGS. 8 and 9 together, the brake clip 94 includes a cylindrical hub 96 and at least one brake arm 98 (two shown in the embodiment of FIGS. 8 and 9). The hub 96 includes a radially outward-facing surface 100 and threads 102 projecting from a radially-inward facing surface 104. Once installed, each of the at least one brake arm 98 extends radially outward from the hub 96 and across the fourth axially-facing surface 76 of the second drum 52 to the radially outward-facing surface 82 of the second drum 52, axially from the radially outward-facing surface 82 to the radially outward-facing surface 62 of the first drum 50 (FIG. 4), and radially inward from the radially outward-facing surface 62 and across a portion of the second axially-facing surface 56 of the first drum 50 (FIG. 3).

Although not illustrated, the braking knob 34 includes a cylindrical braking shaft 106. The braking shaft 106 projects from the braking knob 34 and into the interior of the handle 12. The braking shaft 106 may include threads 108 projecting from a radially outward-facing surface 110. The threads 108 of the braking shaft 106 are configured to threadedly engage the threads 102 projecting from the radially-inward facing surface 104 of the hub 96. So configured, rotation of the braking shaft 106 by the braking knob 34 in, for example, a clockwise direction, may force the brake clip 94 in the direction of the interior surface of handle 12 to which the friction plate 92 is attached. As the brake clip 94 is forced toward the interior surface of handle 12, the at least one brake arm 98 forces the fourth axially-facing surface 76 of the second drum 52 against the friction plate 92, increasing a frictional force between the friction plate 94 and the fourth axially-facing surface 76. The rotation of the braking shaft 96 in the other direction, for example, counterclockwise, may move the friction plate 92 and the fourth axially-facing surface 76 away from one another so as to decrease the frictional force between the friction plate 92 the fourth axially-facing surface 76.

The brake clip 94 may be made of a strong, but somewhat flexible material, for example a metal such as aluminum, or a polymer such as polyetherimide or polyether ether ketone. The radially inward extent of the brake arm 98 across the portion of the second axially-facing surface 56 is suitably sized so that the brake clip 94 may snap into position when installed, and still be useful in pressing against the first drum 50 to increase the frictional force between the friction plate and the fourth axially-facing surface 76.

Although the embodiment described above describes a clockwise rotation of the braking knob 34 to increase the frictional force and a counterclockwise rotation to decrease the frictional force, it is understood that embodiments can include the reverse configuration by reversing the direction of the threads 102 and 108. In addition, while the embodiment above is described with the frictional force formed between the friction plate 92 and the fourth axially-facing surface 76, it is understood that embodiments can include configurations in which the frictional force is formed between the friction plate 92 and the second axially-facing surface 56.

In some embodiments, the braking knob 34 and the braking shaft 106 may be made from a hard plastic, for example, a glass-filled polycarbonate or a polyoxymethylene. In some embodiments, the braking knob 34 and the braking shaft 106 may be integrally formed by, for example, injection molding, to form a single piece.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A steering control apparatus substantially contained within a handle at a proximal end of a catheter to control deflection of a distal end of the catheter, the distal end including a therapy device, the steering control apparatus comprising:
   a first wire extending from the distal end of the catheter to within the handle;
   a second wire extending from the distal end of the catheter to within the handle; and
   a steering assembly including:
      a steering knob disposed at an exterior of the handle;
      a cylindrical steering shaft projecting from the steering knob and into the interior of the handle;
      a first cylindrical drum disposed within the handle and connected to the first wire, the first drum configured to engage the steering shaft to produce tension on the first wire, wherein the first drum is coaxial with the steering shaft; and
      a second cylindrical drum within the handle and connected to the second wire, the second drum configured to engage the steering shaft to produce tension on the second wire, wherein the second drum is coaxial with the steering shaft and axially adjacent to the first drum;

wherein rotation of the steering shaft by the steering knob in a counterclockwise direction steers the distal end of the catheter in the second direction by increasing tension on the first wire and decreasing tension on the second wire, and rotation of the steering shaft by the steering knob in a clockwise direction steers the distal end in the first direction by decreasing tension on the first wire and increasing tension on the second wire.

2. The apparatus of claim 1, wherein:

the steering shaft includes plurality of splines projecting from a radially outward-facing surface of the steering shaft, the splines oriented in an axial direction;

the first drum includes a radially inward-facing surface and a plurality of splines projecting from the inward-facing surface, the splines oriented in an axial direction and configured to engage the plurality of splines on the external surface of the steering shaft to produce the tension on the first wire; and the second drum includes a radially inward-facing surface and a plurality of splines on the inward-facing surface, the splines oriented in an axial direction and configured to engage the plurality of splines on the external surface of the steering shaft to produce the tension on the second wire.

3. The apparatus of claim 1, wherein the first drum further includes a first recess formed in an axial-facing surface, and a first groove extending from the recess and circumferentially around a portion of a radially outward-facing surface of the first drum; and the first wire includes a first lug connected to a proximal end of the first wire, wherein the first lug is disposed in the first recess and a portion of the first wire is disposed within a least a portion of the first groove to connect the first drum to the first wire.

4. The apparatus of claim 3, wherein the second drum further includes a second recess formed in an axial-facing surface, and a second groove extending from the recess and circumferentially around a portion of a radially outward-facing surface of the second drum; and the second wire includes a second lug connected to a proximal end of the second wire, wherein the second lug is disposed in the second recess and a portion of the second wire is disposed within a least a portion of the second groove to connect the second drum to the second wire.

5. The apparatus of claim 4, wherein the axial-facing surface of the first drum including the first recess faces the axial-facing surface of the second drum including the second recess.

6. The apparatus of claim 5, wherein the first drum is directly connected to the second drum.

7. The apparatus of claim 1, wherein the steering knob and the steering shaft are integrally formed.

8. The apparatus of claim 1, further including a brake assembly, the brake assembly including:

a friction plate disposed on an interior surface of the handle;

a brake clip configured to engage the first drum and the second drum; and a braking knob disposed at the exterior of the handle on a side of the handle opposite the steering knob, the braking knob including a cylindrical braking shaft projecting from the braking knob and into the interior of the handle; the braking knob configured to engage the brake clip, wherein rotation of the braking shaft by the braking knob in one of a clockwise direction and a counterclockwise direction increases a frictional force between the friction plate and one of an axially facing surface of the first drum and an axially facing surface of the second drum; and rotation of the braking shaft by the braking knob in the other one of the clockwise direction and the counterclockwise direction decreases the frictional force between the friction plate and the one of the axially facing surface of the first drum and the axially facing surface of the second drum.

9. The apparatus of claim 8, wherein:

the brake clip includes:

a cylindrical hub including:

a radially outward-facing surface, the radially outward-facing surface facing a radially inward-facing surface of the steering shaft; and threads projecting from a radially inward-facing surface of the hub; and at least one brake arm extending radially outward from the hub and across the axially-facing surface of the second drum to the radially outward-facing surface of the second drum, axially from the radially outward-facing surface of the second drum to the radially outward-facing surface of the first drum, and radially inward from the radially outward-facing surface of the first drum and across a portion of the axially-facing surface of the first drum; and the braking knob further includes threads projecting from a radially outward-facing surface of the braking shaft, wherein the threads of the braking shaft are configured to engage the threads of the hub.

10. The apparatus of claim 9, wherein the braking knob and the braking shaft are integrally formed.

11. A catheter comprising:

an elongate catheter body extending from a proximal end to a distal end, wherein the distal end is steerable in a first direction and a second direction, the second direction different from the first direction;

a therapy device connected to the distal end of the catheter body;

a handle connected to the proximal end of the catheter body; and a steering control mechanism disposed at least partially within the handle, the mechanism including:

a first wire extending from the distal end of the catheter to within the handle;

a second wire extending from the distal end of the catheter to within the handle; and a steering assembly including:

a steering knob disposed at an exterior of the handle;

a cylindrical steering shaft projecting from the steering knob and into the interior of the handle;

a first cylindrical drum disposed within the handle and connected to the first wire, the first drum configured to engage the steering shaft to produce tension on the first wire, wherein the first drum is coaxial with the steering shaft; and a second cylindrical drum within the handle and connected to the second wire, the second drum configured to engage the steering shaft to produce tension on the second wire, wherein the second drum is coaxial with the steering shaft and axially adjacent to the first drum;

wherein rotation of the steering shaft by the steering knob in a counterclockwise direction steers the distal end of the catheter in the second direction by increasing tension on the first wire and decreasing tension on the second wire, and rotation of the steering shaft by the steering knob in a clockwise direction steers the distal end in the first direction by decreasing tension on the first wire and increasing tension on the second wire.

12. The catheter of claim 11, wherein:
the steering shaft includes plurality of splines projecting from a radially outward-facing surface of the steering shaft, the splines oriented in an axial direction;
the first drum includes a radially inward-facing surface and a plurality of splines projecting from the inward-facing surface, the splines oriented in an axial direction and configured to engage the plurality of splines on the external surface of the steering shaft to produce the tension on the first wire; and
the second drum includes a radially inward-facing surface and a plurality of splines on the inward-facing surface, the splines oriented in an axial direction and configured to engage the plurality of splines on the external surface of the steering shaft to produce the tension on the second wire.

13. The catheter of claim 11, wherein the first drum further includes a first recess formed in an axial-facing surface, and a first groove extending from the recess and circumferentially around a portion of a radially outward-facing surface of the first drum; and the first wire includes a first lug connected to a proximal end of the first wire, wherein the first lug is disposed in the first recess and a portion of the first wire is disposed within a least a portion of the first groove to connect the first drum to the first wire.

14. The catheter of claim 13, wherein the second drum further includes a second recess formed in an axial-facing surface, and a second groove extending from the recess and circumferentially around a portion of a radially outward-facing surface of the second drum; and the second wire includes a second lug connected to a proximal end of the second wire, wherein the second lug is disposed in the second recess and a portion of the second wire is disposed within a least a portion of the second groove to connect the second drum to the second wire.

15. The catheter of claim 14, wherein the axial-facing surface of the first drum including the first recess faces the axial-facing surface of the second drum including the second recess.

16. The catheter of claim 11, wherein the steering knob and the steering shaft are integrally formed.

17. The catheter of claim 11, wherein the steering control mechanism further includes a brake assembly, the brake assembly including:

a friction plate disposed on an interior surface of the handle;
a brake clip configured to engage the first drum and the second drum; and
a braking knob disposed at the exterior of the handle on a side of the handle opposite the steering knob, the braking knob including a cylindrical braking shaft projecting from the braking knob and into the interior of the handle; the braking knob configured to engage the brake clip, wherein rotation of the braking shaft by the braking knob in one of a clockwise direction and a counterclockwise direction increases a frictional force between the friction plate and one of an axially facing surface of the first drum and an axially facing surface of the second drum; and rotation of the braking shaft by the braking knob in the other one of the clockwise direction and the counterclockwise direction decreases the frictional force between the friction plate and the one of the axially facing surface of the first drum and the axially facing surface of the second drum.

18. The catheter of claim 17, wherein:
the brake clip includes:
a cylindrical hub including:
a radially outward-facing surface, the radially outward-facing surface facing a radially inward-facing surface of the steering shaft; and
threads projecting from a radially inward-facing surface of the hub; and
at least one brake arm extending radially outward from the hub and across the axially-facing surface of the second drum to the radially outward-facing surface of the second drum, axially from the radially outward-facing surface of the second drum to the radially outward-facing surface of the first drum, and radially inward from the radially outward-facing surface of the first drum and across a portion of the axially-facing surface of the first drum; and
the braking knob includes threads projecting from a radially outward-facing surface of the braking shaft, wherein the threads of the braking shaft are configured to engage the threads of the hub.

19. The catheter of claim 17, wherein the braking knob and the braking shaft are integrally formed.

20. The catheter of claim 11, wherein catheter is a cardiac mapping catheter and the therapy device includes a mapping electrode array.

* * * * *